United States Patent [19]

Metala et al.

[11] Patent Number: 5,061,364
[45] Date of Patent: Oct. 29, 1991

[54] DIAGNOSTIC FILTER FOR DETECTING CONDUCTIVE AND SEMICONDUCTIVE PARTICLES IN A FLUID STREAM

[75] Inventors: Michael J. Metala, Murrysville; William G. Clark, Jr., Murrysville Boro, both of Pa.

[73] Assignee: Westinghouse Electric Corp., Pittsburgh, Pa.

[21] Appl. No.: 470,471

[22] Filed: Jan. 26, 1990

[51] Int. Cl.⁵ ............................................. B01D 35/14
[52] U.S. Cl. ...................................... 210/85; 55/270; 324/204; 324/233; 73/7; 73/64; 384/448; 210/251
[58] Field of Search ......................... 210/85, 746, 251; 324/204, 226, 233; 340/631; 384/8, 448; 73/7, 64, 861.04; 123/198 DA; 184/6.4, 108; 55/270

[56] References Cited

U.S. PATENT DOCUMENTS

| | | | |
|---|---|---|---|
| 3,186,549 | 6/1965 | Botstiber | 210/86 |
| 3,317,042 | 5/1967 | Botstiber | 210/86 |
| 3,325,009 | 6/1967 | Botstiber et al. | 210/86 |
| 3,686,926 | 8/1972 | Miller et al. | 73/61 R |
| 3,748,576 | 7/1973 | Sigournay | 73/861.41 |
| 3,878,103 | 4/1975 | Miller et al. | 210/243 |
| 4,176,545 | 12/1979 | Oddo | 324/204 |
| 4,279,748 | 7/1981 | Inoue | 210/85 |
| 4,486,713 | 12/1984 | Gifford | 324/233 |
| 4,620,185 | 10/1986 | Plahmer | 340/682 |
| 4,658,638 | 4/1987 | Plahmer | 340/682 |
| 4,756,824 | 7/1988 | Howard, Jr. et al. | 210/85 |
| 4,837,511 | 6/1989 | Whittington et al. | 324/204 |

FOREIGN PATENT DOCUMENTS 0038115  4/1981  Japan .

Primary Examiner—Robert A. Dawson
Assistant Examiner—Matthew O. Savage
Attorney, Agent, or Firm—K. Bach

[57] ABSTRACT

A diagnostic filter device for monitoring electrically conductive and semiconductive particles entrained by a fluid, composed of:

a filter element (4) disposed to receive the fluid and to permit passage of the fluid while retaining particles entrained in the fluid;

a component (8) disposed for producing an alternating electromagnetic field which extends across at least one region of the filter element (4); and an eddy current detecting instrument (12) connected to the electromagnetic field producing component (8) for detecting the influence on the field of particles in the filter element region.

11 Claims, 2 Drawing Sheets

DIAGNOSTIC FILTER FOR DETECTING CONDUCTIVE AND SEMICONDUCTIVE PARTICLES IN A FLUID STREAM

BACKGROUND OF THE INVENTION

The present invention relates to a novel system which cooperates with a filter in order to detect and identify particles of conductive or semiconductive materials entrained in a fluid stream.

In the case of many forms of mechanical apparatus, such as heavy machinery, in which lubricant systems are provided to prolong the operating lifetime, it is desirable to monitor the wear of critical parts. Such monitoring permits preventive maintenance to be scheduled in an optimum manner.

It has long been the practice to carry out detailed chemical and physical analyses of oil samples removed from lubrication systems in order to obtain such wear determinations. Such analyses are performed in order to determine the composition and quantity of particles in the oil sample, on the basis of which component wear as a function of operating conditions can be identified and evaluated.

Other techniques which have been recently developed allow for more rapid analyses of lubricant samples. One such method, known as ferrography, can be employed to measure the presence of ferromagnetic particles. This technique involves the use of a permanent magnet on which the particles accumulate and a magnetometer to measure the quantity of particles collected. This technique can be employed under on-line, real time conditions and eliminates the need to collect and analyze separate samples.

Other techniques which have been proposed also involve the use of magnets to collect samples and the provision of a detection circuit which produces an output when the quantity of samples collected completes an electric current path.

All of the techniques described above are limited to the detection and analysis of ferromagnetic particles. This severely limits the applications of such techniques because most sophisticated machinery installations in which real time diagnostics are desirable employ a wide variety of non-ferromagnetic materials.

SUMMARY OF THE INVENTION

It is a primary object of the present invention to carry out on-line, real time wear analyses with respect to apparatus in which wear is evidenced by the production of non-ferromagnetic conducting and semiconducting materials.

A more specific object of the invention is to provide on-line determinations of both the composition and quantity of non-ferromagnetic particles entrained in a fluid stream.

The above and other objects are achieved, according to the present invention, by a diagnostic filter device for monitoring electrically conductive and semiconductive particles entrained by a fluid, comprising:
a filter element disposed to receive the fluid and to permit passage of the fluid while retaining particles entrained in the fluid;
means disposed for producing an alternating electromagnetic field which extends across at least one region of the filter element; and
eddy current detecting means connected to the electromagnetic field producing means for detecting the influence on the field of particles in the filter region.

In a device according to the present invention, an electromagnetic field is produced in a region in which particles constituting impurities in a fluid stream are collected so that the particles, if they are of an electrically conductive or semiconductive material, will alter the effective impedance of the device producing the electromagnetic field. By monitoring such impedance variations, the composition and concentration of such particles can be determined in real time and in a nondestructive manner.

The specific response produced will depend on the geometry and field activation parameters of the element producing the electromagnetic field, as well as on the material properties of the particles and the distribution of the particles within the electromagnetic field. Under controlled conditions, an eddy current test can produce indications of the electrical conductivity and magnetic permeability of a conducting or semiconducting material. This permits material identification and alloy sorting to be achieved with a structurally simple arrangement.

DESCRIPTION OF THE PREFERRED EMBODIMENTS

Figure 1:
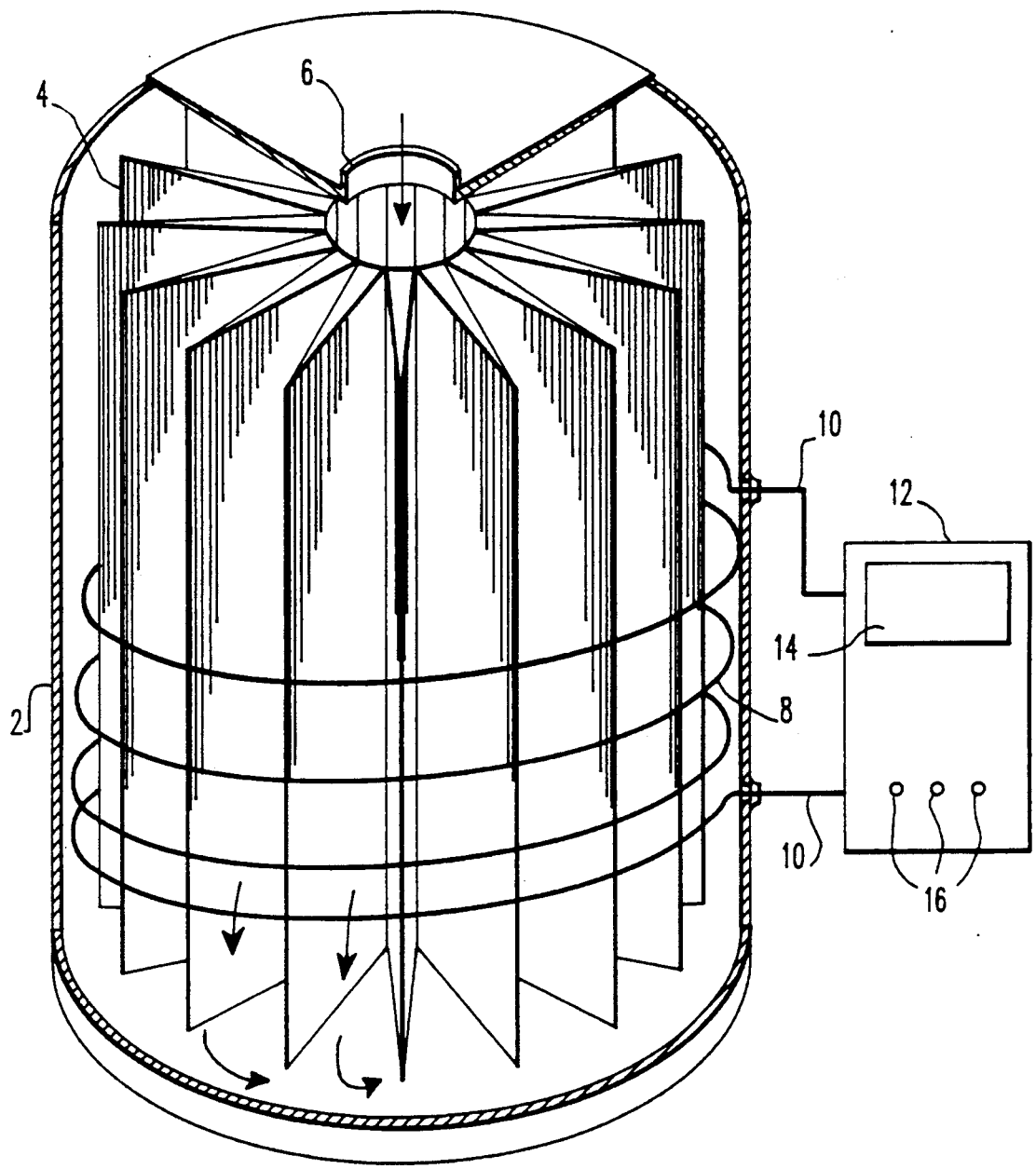
FIG. 1 is a perspective view of a preferred embodiment of the present invention.

FIG. 1 is a perspective view illustrating one preferred embodiment of a diagnostic filter device according to the invention. The device shown in FIG. 1 includes a casing 2 containing a cylindrical, pleated filter element 4, which may be made of a paper or fibrous material having a selected porosity. Filter element 4 encloses a generally cylindrical space into which fluid is introduced via an inlet tube 6 forming part of casing 2 and communicating with the interior of filter element 4. Fluid introduced to the interior of filter element 4 flows axially along filter element 4 and radially outwardly through filter element 4 to the region of casing 2 surrounding filter element 4. This fluid exits through an outlet (not shown) provided in the bottom of casing 2.

According to the invention, filter element 4 is surrounded by a coil of wire 8 having input/output leads 10. Leads 10 are connected to a known eddy current test instrument 12 having a cathode ray display 14 and calibration dials 16.

Instrument 12 can be constituted by any suitable commercially available eddy current instrument. By way of example, this could be constituted by an instrument marketed by the Hocking Company of Herefordshire, England, under the model designation AV10.

Prior to being placed in use, with no conductive or semiconductive material within filter element 4, instrument 12 may be calibrated to produce a zero display. Thereafter, fluid containing particles of conductive or semiconductive material is caused to flow through casing 2, whereupon particles of conductive or semiconductive materials enter the electromagnetic field produced by coil 8 and some of these particles become trapped in the folds at the outer periphery of filter element 4. Any particles within the electromagnetic field influence the signals detected by instrument 12, producing, on cathode ray display 14, a trace which is characteristic of the nature and quantity of the particles within the electromagnetic field. The form, including the amplitude, configuration and orientation, of the trace is a function of changes in the effective complex impedance of the coil system due to the conductive or semiconductive particles within the field.

Figure 2:
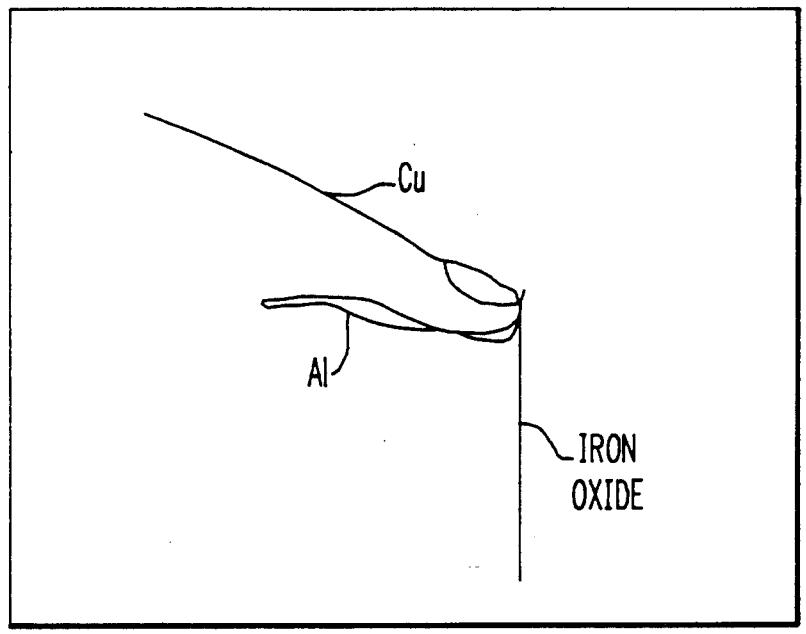
FIG. 2 is a pictorial representation of various displays which can be produced with a device according to the present invention.

FIG. 2 illustrates the traces which have been obtained on display 14, after initial calibration as described above, for three different impurity materials: copper, aluminum and iron oxide. For a given material, the phase angle detected by instrument 12, corresponding to the direction of the trace on display 14, is a function of the material composition, and the amplitude of the detected signal, corresponding to the length of the trace on display 14, is proportional to the quantity of impurity material in the coil field. Material composition can be determined with reasonable reliability if particles of a single material are present in the fluid flowing through filter element 4. The concentration of particles in the stream, corresponding to the rate at which particles collect in filter element 4, can be determined by measuring the length of the trace on display 14 at fixed time intervals. The traces shown in FIG. 2 where obtained by producing in coil 8 an electromagnetic field at a frequency of 5 MHz.

A diagnostic filter according to the present invention can be used for monitoring material failure or wear in a wide variety of systems which are cooled or lubricated by, or which transport, an electrically nonconductive liquid. These include simple lubrication systems or virtually any pump, valve or plumbing system. The invention can be applied to the monitoring of condenser and boiler tubing. Diagnostic filters according to the invention could be disposed at strategic locations to individually monitor special problem areas. Oil and natural gas pipeline systems composed of a large number of remote pumping stations could be equipped with diagnostic filters for monitoring a variety of components. Diagnostic filters according to the invention could be applied to actuator systems of the type employed in aerospace applications and containing nonferrous metals. In addition, the invention could be applied for monitoring compressor systems for cooling equipment as well as turbo chargers and superchargers for automotive applications.

For all such applications, it is preferable that the region occupied by the electromagnetic field not contain any parts of conductive or semiconductive material. However, in certain cases, if parts of such materials are present, it may be possible to nullify the influence of those parts by the initial zeroing of the eddy current instrument.

According to one possibility contemplated by the invention, the surface of a body which is exposed to the fluid stream and which is subject to wear may be provided with a coating containing particles which will produce a defined eddy current instrument response.

According to another possibility, such surface may be coated with successive layers of respectively different conductive or semiconductive materials each producing a distinctly different eddy current response. Then a change in the response of the eddy current instrument will serve to indicate that one layer has been worn through.

Figure 3:
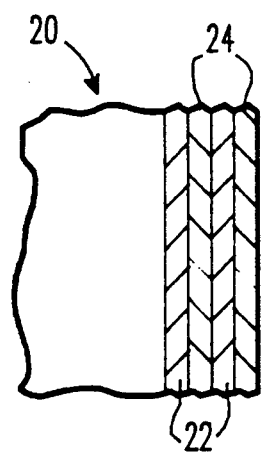
FIG. 3 is a cross-sectional view of the surface of a boy which is to be monitored according to the invention.

FIG. 3 illustrates a surface of a part 20 to be monitored provided with a plurality of coating layers including layers 22 consisting of or containing a first nonferrous material alternating with layers 24 consisting of or containing a second nonferrous material selected to produce an eddy current instrument response different from that produced by the first material. As each layer wears away, particles from the underlying layer will enter the lubricant stream and become trapped within filter element 4. As particles of a second type build up in filter element 4, the direction of the trace produced on display 14 will begin to change. The wear experienced by the layer structure of FIG. 3 could also be monitored by periodically recording the parameters of the display and zeroing the display after each recording. Then, when particles begin to wear away from a new layer, the direction of the trace on the display will change in a clearly observable manner. According to one embodiment of the arrangement shown in FIG. 3, each layer 22 could consist of or contain particles of, copper, while each layer 24 could consist of, or contain particles of, iron oxide. Other pairs of materials could also be selected Furthermore, while FIG. 1 illustrates one effective embodiment of a filter element 4, it will be appreciated that filter elements having other configurations could be employed.

It should additionally be appreciated that the diagnostic filter according to the invention may be used to detect particles of ferrous materials. However, a significant advantage of the invention resides in its ability to detect nonferrous particles.

It should further be noted that devices according to the present invention can employ a simple bridge circuit, possibly with a go-no-go visual indicator, to provide an indication of changes in the effective impedance of the sensing coil.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A diagnostic filter device for monitoring electrically conductive and semiconductive particles entrained by a fluid, comprising:
   a filter element disposed to receive the fluid and to permit passage of the fluid while retaining particles entrained in the fluid;
   means disposed for producing an alternating electromagnetic field which extends across at least one region of said filter element; and
   eddy current detecting means connected to said electromagnetic field producing means for detecting the influence of particles in said filter element region on said field, in combination with a body having a surface exposed to the fluid at a location upstream of the filter element region, wherein said body surface comprises a first layer containing a first conductive or semiconductive material which can influence said field in a first manner which causes said eddy current detecting means to produce a first observable detection result an a second layer superposed on said first layer and containing a second conductive or semiconductive material different form said first material and which can influence said field in a second manner which causes said eddy current detecting means to produce a second observable detection result observably different from the first detection result.

2. The combination as defined in claim 1 wherein said filter element as the form of a hollow cylinder and said field producing means comprise an inductive coil surrounding said cylinder and having an inherent inductive impedance.

3. The combination as defined in claim 2 wherein said filter element is pleated to have a plurality of crevices in which particles can accumulate.

4. The combination as defined in claim 3 wherein said filter element is made of an electrically nonconductive material.

5. The combination as defined in claim 2 wherein said filter element is made of an electrically nonconductive material.

6. The combination as defined in claim 2 wherein the region enclosed by said coil is free of electrically conductive or semiconductive material other than the particles to be monitored.

7. The combination as defined in claim 1 wherein said eddy current detecting means comprise an instrument having an electrical power source connected for supplying the alternating current to said field producing means, and having a cathode ray tube connected to produce a display representative of the effective impedance of said field producing means.

8. The combination as defined in claim 7 wherein said instrument further comprises means for nulling the display produced by said cathode ray tube.

9. The combination defined in claim 1 wherein said first layer constitutes an integral part of said body.

10. A diagnostic filter device for monitoring electrically conductive and semiconductive particles entrained by a fluid, comprising:

a filter element disposed to receive the fluid and to permit passage of the fluid while retaining particles entrained in the fluid, said filter element having the form of a hollow cylinder made of an electrically nonconductive material which is pleated to have a plurality of crevices in which particles can accumulate;

means comprising an inductive coil surrounding said cylinder and having an inherent complex inductive impedance for producing an alternating electromagnetic field which extends across at least one region of said filter element; and eddy current detecting means connected to said electromagnetic field producing means for detecting the influence of particles in said filter element region of said field, said eddy current detecting means comprising an instrument having: an electrical power source connected for supplying operating power to said coil; a cathode ray tube connected to produce a display representative of the effective complex impedance of said electromagnetic field producing means; and means for nulling the display produced by said cathode ray tube;

wherein the region enclosed by said coil is free of electrically conductive or semiconductive material other than the particles to be monitored.

in combination with a body having a surface exposed to the fluid at a location upstream of the filter element region, wherein said body surface comprises a first layer containing a first conductive or semiconductive material which can influence said field in a first manner and a second layer superposed on said first layer and containing a second conductive or semiconductive material different from said first material and which can influence said field in a second manner different from the first manner.

11. The combination defined in claim 10 wherein said first layer constitutes an integral part of said body.

* * * * *